United States Patent [19]

McManus et al.

[11] Patent Number: 5,686,613

[45] Date of Patent: Nov. 11, 1997

[54] TRIDENTATE METAL LIGANDS OF CERTAIN PYRIDINE PHOSPHONIC ACIDS

[75] Inventors: Derek McManus, Roselle, Ill.; Arthur E. Martell, College Station; Dian Chen, Bryan, both of Tex.

[73] Assignee: Wheelabrator Clean Air Systems Inc., Schaumburg, Ill.

[21] Appl. No.: 585,538

[22] Filed: Jan. 16, 1996

[51] Int. Cl.[6] ................................ C07F 9/58; C07F 1/08; C07F 3/06

[52] U.S. Cl. ........................... 546/5; 546/6; 546/21

[58] Field of Search ............................. 546/5, 6, 21

[56] References Cited

U.S. PATENT DOCUMENTS

| | | | |
|---|---|---|---|
| 4,011,304 | 3/1977 | Mancini et al. | 423/576.6 |
| 4,189,462 | 2/1980 | Thompson | 423/576.6 |
| 4,238,462 | 12/1980 | Hardison | 423/576.6 |
| 4,622,212 | 11/1986 | McManus et al. | 423/226 |
| 5,139,753 | 8/1992 | Hardison | 423/220 |
| 5,273,734 | 12/1993 | Sawyer et al. | 423/573.1 |

OTHER PUBLICATIONS

Chemical Abstracts, Vo.78(No.6) abst.No.37,329a Feb. 12, 1973.

Chemical Abstracts, vol. 104(No. 18), abst.No.160,892m May 5, 1986.

Chemical Abstracts, Vo.103(No.18), abst.No.148,128p, Nov. 4, 1985.

Chemical Abstracts, vol. 102(No. 13), abst. No. 124,498n, Apr. 1, 1985.

Chemical Abstracts, vol. 102(No. 12), abst. No. 105,084h, Mar. 25, 1985.

Young-Shen Huang et al., Polyhedron, vol. 10. No. 19, pp. 2229–2233, Dec. 1991.

*Oxidation of $H_2S$ to S by Air With Fe(III)–NTA as a Catalyst: Catalyst Degradation*; By Dian Chen, Ramunas J. Motekaitis, Arthur E. Martell, and Derek McManus; Canadian Journal of Chemistry, vol. 71, pp. 1524–1531, 1993.

*Primary Examiner*—Alan L. Rotman
*Attorney, Agent, or Firm*—McDonnell Boehnen et al.

[57] ABSTRACT

Novel pyridine phosphonate ligands are disclosed that when combined with polyvalent metals results in useful catalyst compositions for the conversion of hydrogen sulfide to solid sulfur. Catalysts containing these novel ligands exhibit resistance to metal precipitation and demonstrate little or no oxidative chemical degradation when employed to convert hydrogen sulfide to elemental sulfur.

6 Claims, 5 Drawing Sheets

| ORGANIC STARTING MATERIALS | REAGENTS | |
|---|---|---|
| $\bigcirc_{N}\text{—COOH}$ PICOLINIC ACID | $CH_3COOH$ | GLACIAL ACETIC ACID |
| | $H_2O_2$ | HYDROGEN PEROXIDE |
| | $(CH_3)_2SO_4$ | DIMETHYL SULFATE |
| $\bigcirc_{N}$ PYRIDINE | $LiC_4H_9$ | BUTYLLITHIUM |
| | $(C_2H_5O)_2\overset{O}{\underset{\|}{P}}H$ | DIETHYLPHOSPHITE |

TRIDENTATE METAL LIGANDS OF CERTAIN PYRIDINE PHOSPHONIC ACIDS

FIELD OF THE INVENTION

This invention relates to new chemical compounds comprising pyridine phosphonates. These compounds are especially useful in preparing coordination compounds, such as chelates. The resulting chelates are extremely useful as catalysts in oxidation-reduction processes, in particular the conversion of $H_2S$ to solid sulfur.

BACKGROUND OF THE INVENTION

Ligands, also known as complexing agents, can be any molecule, atom, or ion that is attached to the central atom of a coordination compound. For example, the ammonia molecule in $[Co(NH_3)_6]^{3+}$ and the chlorine atoms in $PtCl_4$ are ligands. Commercially, ligands are used to modify the properties of metals or metal ions. Ligands interact differently with different metal ions thus producing surprising and unexpected properties for the resulting coordination compounds. Ligands with two or more donor atoms coordinated to the same acceptor atom are known as chelating ligands.

The combination of chelating ligands with metals, such as, iron, copper, cobalt, nickel or manganese results in the formation of metal chelates useful as catalysts in the oxidation-reduction processes to convert $H_2S$ to solid sulfur.

Hydrogen sulfide and alkyl mercaptans are a major source of pollution of air streams since they are liberated as waste by-products in a number of chemical processes, such as sulfate or kraft paper pulp manufacture, viscose manufacture, sewage treatment, sulfurretting fatty oils, and production of organic compounds, as well as in petroleum refining and in the production of natural gas and of combustible gases from coal, such as in coking operations. These sulfur compounds are also present in geothermal steam used in power generating plants.

The use of an aqueous chelated metal catalyst solution for removing hydrogen sulfide from a gas stream is well known in the art. However, those processes relied on chelating ligands such as amino and/or polyaminopolyacetic acids, e.g. nitrilotriacetic acid, ethylenediaminetetraacetic acid, N-hydroxyethyl ethylenediamine triacetic acid, and diethylenetriamine pentaacetic acid and alkali metal salts thereof. In those prior art processes a chelated metal catalyst solution is contacted with hydrogen sulfide-containing gas, known as "sour gas", to effect oxidation of the hydrogen sulfide to elemental sulfur and concomitant reduction of the metal chelate to a lower oxidation state. The catalyst solution is then regenerated for reuse by contacting it with an oxygen-containing gas to oxidize the metal chelate to a higher oxidation state. The elemental sulfur is continuously removed from the process as a solid product with high purity. Illustrative of these oxidation-reduction processes is the description contained in U.S. Pat. No. 4,622,212 (McManus et al.) and the references cited therein.

While the processes, and their associated catalyst composition, described in the art have achieved sufficient efficiency and stability for commercial utilization, a need still exists for alternate and significantly more stable catalyst systems. This invention addresses this need and in particular provides catalyst solutions having more stability against in-process oxidative degradation of the active metal chelate. It also significantly reduces metal sulfide precipitation, even when substoichiometric iron to sulfur mole ratios are present in the absorber section of the process. This invention also increases the stability of the metal chelating compound against hydrolysis in aqueous solutions having pH values up to and above 9.0. These and other advantages will become evident from the following more detailed description of the invention.

SUMMARY OF THE INVENTION

Accordingly, in one embodiment, the invention relates to new ligands having the following formulae:

where, R is COOH or $PO(OH)_2$ and $R_1$, $R_2$ and $R_3$ is each selected independently from the group consisting of H, OH, alkyl containing 1 through 3 carbon atoms, $NO_2$, $SO_3H$, Cl, Br, F, and CN.

Still another embodiment of the invention relates to a process for the conversion of $H_2S$ to sulfur in which the $H_2S$ is contacted under conditions to convert $H_2S$ with a solution containing an effective amount of a polyvalent metal chelate composition of the formula described above. Preferred catalyst compositions for the removal of hydrogen sulfide from waste gas streams have the following formulas: ML and $ML_2$ where L has one of the following formulas:

and where M is a polyvalent metal selected from the group consisting of iron, copper, cobalt, nickel and manganese. A preferred polyvalent metal is iron and the series of reactions involved in catalytically oxidizing hydrogen sulfide to elemental sulfur using an iron chelate catalyst can be represented by the following reactions, where L represents either one of the pyridine based ligands described above:

(1) $H_2S\ (gas) + H_2O(liq.) \rightleftharpoons H_2S\ (aqueous) + H_2O(liq.)$
(2) $H_2S\ (aqueous) \rightleftharpoons H^+ + HS^-$
(3) $HS^- + 2(Fe^{3+}L_2) \rightarrow S\ (solid) + 2(Fe^{2+}L_2) + H^+$ By combining equation (1) through (3) the resulting equation is:

(4) $H_2S\ (gas) + 2(Fe^{3+}L_2) \rightarrow 2H^+ + 2(Fe^{2+}L_2) + S\ (solid)$

In order to have an economical workable process for removing hydrogen sulfide from a gaseous stream when a ferric iron chelate is used to effect catalytic oxidation of the hydrogen sulfide, it is essential that the ferrous iron chelate formed in the above described manner be continuously regenerated by oxidizing to ferric iron chelate on contacting the reaction solution with dissolved oxygen, preferably in the form of ambient air, in the same or in a separate contact zone. The series of reactions which take place when regenerating the metal chelate catalyst can be represented by the following equations:

(5) $O_2\ (gas) + 2H_2O \rightleftharpoons O_2\ (aqueous) + 2H_2O$
(6) $O_2\ (aqueous) + 2H_2O + 4(Fe^{2+}L_2) \rightarrow 4(OH^-) + 4(Fe^{3+}L_2)$ By combining equations (5) through (6), the resulting equation (7) is:

(7) ½ $O_2 + H_2O + 2(Fe^{2+}L_2) \rightarrow 2(OH^-) + 2(Fe^{3+}L_2)$

And, when equations (4) and (7) are combined, the overall process can be represented by the following equation:

(8) $H_2S$ (gas) + ½ $O_2$ (gas) → S (solid) + $H_2O$ (liq.)

As gaseous hydrogen sulfide has a low solubility in an acidic aqueous solution, the catalytic oxidation of the hydrogen sulfide is preferably carried out in an aqueous alkaline solution because hydrogen sulfide gas is absorbed more rapidly and hydrosulfide ions are produced at significantly increased rates when the reaction solution has a higher pH value. When the continuous catalytic oxidation-reduction reaction solution is maintained at the higher pH values and a conventional chelating agent used, an insoluble precipitate of ferric hydroxide is formed which removes iron from the reaction solution and reduces the concentration of catalytic reagent. The precipitation of ferrous sulfide is likewise highly detrimental, as this also reduces the concentration of the catalytic reagent in the reaction solution and fouls both the sulfur product and process equipment. It is therefore desirable to eliminate or minimize the loss of iron from the reaction solution, particularly at the higher pH values, in order to improve the process for removing hydrogen sulfide from a stream of industrial process gas.

It has been found that not all iron chelating agents capable of forming a complex in aqueous solutions with iron in the ferric valence state ($Fe^{3+}$) or in the ferrous valence state ($Fe^{2+}$) are suitable for use over the broad range of operating conditions employed for this oxidation-reduction system for the removal of hydrogen sulfide.

Among the iron chelate reagents which have been used in prior art processes for removing hydrogen sulfide are the polyaminopolyacetic acid-type chelating agents, such as ethylenediamine tetraacetic acid and the alkali metal salts thereof.

Another chelate compound that has been tried without success is described in U.S. Pat. No. 5,273,734 (Sawyer et al.) and contains a ligand having the following formula:

Wherein R is selected from H and alkyls containing 1 through 3 carbon atoms. Polyvalent metal chelating catalysts made using one specific type of the Sawyer et al. ligand is the iron chelate of 2,6-pyridinedicarboxylic acid, a chelating agent which exhibits good resistance to catalyst degradation but unfortunately experiences unacceptable precipitation of ferric hydroxide from its ferric chelate when operating at the normal pH of the process. Using the ligands of the present invention to prepare polyvalent metal chelate catalyst yields catalyst solutions that resist degradation and do not form appreciable precipitates of ferric hydroxide when operated at basic conditions of pH 9.0 or higher. In addition, conversion of the ferrous complex to iron sulfide is prevented.

Accordingly, a primary object of the present invention is to provide a novel ligand composition useful for preparing polyvalent metal chelate compounds.

It is also an object of this invention to provide a novel and improved catalyst composition for use in oxidation-reduction systems for removing hydrogen sulfide from fluid streams which avoids difficulties encountered in the prior art systems of this type.

Yet another object of the present invention is to provide an improved continuous process for the removal of hydrogen sulfide from a gaseous stream without causing loss of catalyst while operating the process at the most efficient range of pH values.

Finally, still another object is to provide a stable polyvalent metal chelate catalyst that increases the capacity of conventional oxidation-reduction processes which are presently limited by the extent of degradation of the conventionally used chelating agents and relative economics of alternate prior art processes.

DETAILED DESCRIPTION OF PREFERRED EMBODIMENTS

Figure 1:
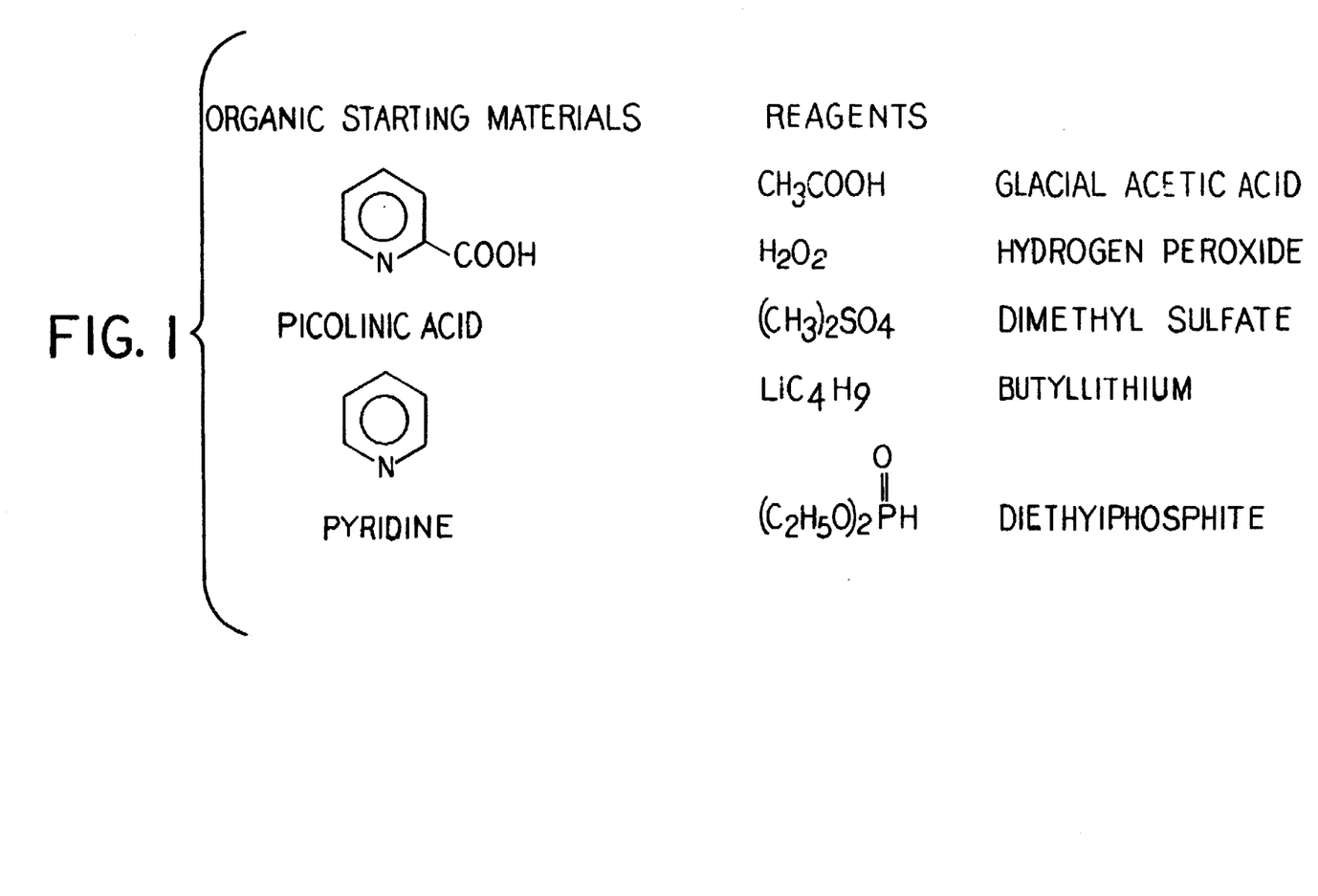
FIG. 1 depicts commercially available compounds that can be used to initiate the synthesis of the ligands of this invention.

The novel chemical compounds of this invention are characterized in that each contains a pyridine group and a phosphonic acid group. Since these ligands are heretofore unknown, and therefore not commercially available, each must be synthesized using a series of chemical reaction steps. Commercially available chemical compounds that can be used as starting materials in the chemical synthesis of these ligands are shown in FIG. 1. Any synthesis procedure known to the art may be used to make a specific ligand from the many different species of ligand that are defined in this invention. Two species in particular have worked extremely well as chelating agents in preparing catalyst for the oxidation of $H_2S$ to solid sulfur.

Figure 2:
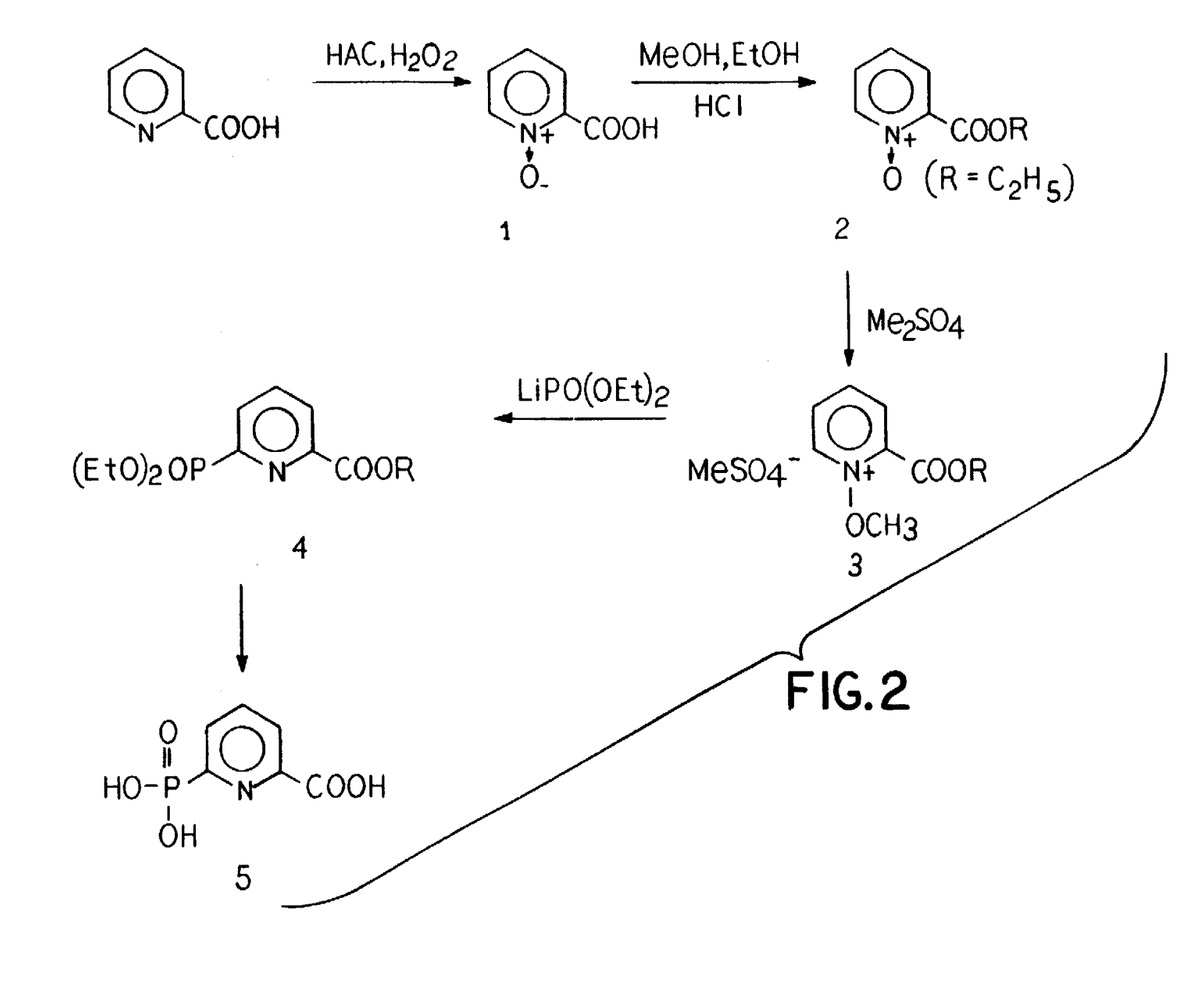
FIG. 2 schematically illustrates a synthesis scheme used to create a preferred embodiment of this invention.

The first of these ligands is pyridine-2-phosphonic-6-carboxylic acid (hereinafter abbreviated as "2P6C"). One method by which 2P6C may be synthesized is illustrated in FIG. 2 and begins with treating picolinic acid (20.0 g) with 125 ml glacial acetic acid and 22 ml 30% $H_2O_2$. The reaction mixture is then heated to 70°–80° C. for 3 hrs. Another 11 ml of 30% $H_2O_2$ solution is then added and the temperature is maintained at 70° C. for 18 hr. Most of the solvent is removed by evaporation, and the residue is cooled to room temperature and allowed to stand in a refrigerator (~5° C.) for 2 hrs. The white solid that precipitates is filtered off and dried at 60° C. under vacuum for 2 hrs. This procedure yields compound 1 of FIG. 2. To 20.3 g of compound 1, 130 ml of EtOH is added and the mixture is treated with HCl gas for 30 minutes. Then the solution is heated to reflux for 30 minutes. The solvent is removed by evaporation under reduced pressure and to the resulting residue, 130 ml of EtOH is added and the above procedure is repeated. Compound 2 is obtained as a white solid and is used directly in the next step. Dimethylsulfate (15.2 g) is slowly added to compound 2 over a 30 minute period. It was then heated at 80°–90° C. for 3 hours to ensure complete reaction. The reaction mixture, a yellow oil, is used directly in the next step. n-Butyllithium (15.0 ml of 23% solution in hexane) is added dropwise to 25 ml of diethylphosphite at −20.0 to 0°

C. over a 2 hr. period. To the resulting solution of lithium diethylphosphite, compound 3 in diethyl phosphite (40 ml) is added over 1 hr. at −15° C. The reaction mixture is stirred at room temperature for 16 hrs. and heated at 70° C. for 2 hrs. After the mixture has cooled to room temperature, 140 ml of water is added. The mixture is then extracted three times with 75 ml $CH_2Cl_2$. The organic extracts are combined and are extracted with 100 ml of 4 M HCl. The organic solvent is removed by evaporation under vacuum. Compound 4 is obtained as a yellow oil. Compound 4 (24.7 g) is heated under reflux with 150 ml concentrated HCl for 16 hrs. After the mixture is allowed to cool to room temperature, the solution is extracted four times with 50 ml $CH_2Cl_2$ and the organic extracts are discarded. The aqueous acid solution is evaporated, treated with a small amount of water and the white solid is filtered off. The residue is washed with a small amount of cold water and compound 5 is produced after drying under a vacuum over $P_2O_5$ for 16 hrs.

The second species of ligand of this invention that shows favorable performance as a part of a catalyst composition for the conversion of $H_2S$ to solid sulfur in waste gas streams is pyridine-2,6-diphosphonic acid (hereinafter abreviated as "2,6-PDPA"). To synthesize 2,6-PDPA, the scheme illustrated in FIG. 3 can be used, where 31.5 ml (0.075 mole) n-butyllithium (23% in hexane) is added dropwise to 12.5 g (0.090 mole) of diethylphosphite at −20.0 to −30.0° C. over a 2 hr. period. To the resulting solution of lithiumdiethylphosphite, compound 1 of FIG. 3, a solution of N-methoxypyridiniummethylsulfate, compound 3, (from 7.15 g (0.075 mole) pyridine N-oxide, compound 2, and 9.5 g (0.075 mole) of dimethylsulfate in diethylphosphite (20 ml) is added at −15.0° C. in 1 hr. The reaction mixture is stirred at room temperature for 16 hrs. then 50 ml of water is added. The mixture is then extracted three times with 38 ml of chloroform, and the organic extracts are combined and extracted with 4N HCl, neutralized with base, and reextracted with chloroform. From this chloroform solution, after distillation 10.8 g of compound 4 is obtained. Compound 4, 10.8 g, 36 ml of glacial acetic acid and 6 ml of hydrogen peroxide are mixed and the reaction mixture is heated to 70.0°–80.0° C. for 3 hrs. Another 3 ml of hydrogen peroxide is added and the temperature is maintained at 70.0 ° C for 16 hrs. The solvent is removed by rotovaporation and to the residue, 100 ml of chloroform is added, the organic phase is washed with concentrated sodium carbonate solution, and then dried with magnesium sulfate for 16 hrs. After the solvent is removed compound 5 is obtained. Dimethylsulfate (4.3 g) is then slowly added to 7.9 g of compound 5 over 30 min. This reaction mixture is heated with a steam-bath for 2 hr. to ensure complete reaction. The compound is purified by silica gel, with a mixed solvent of methylene chloride and methanol used as eluant. After the solvents are removed, compound 6 is obtained.

Figure 3:
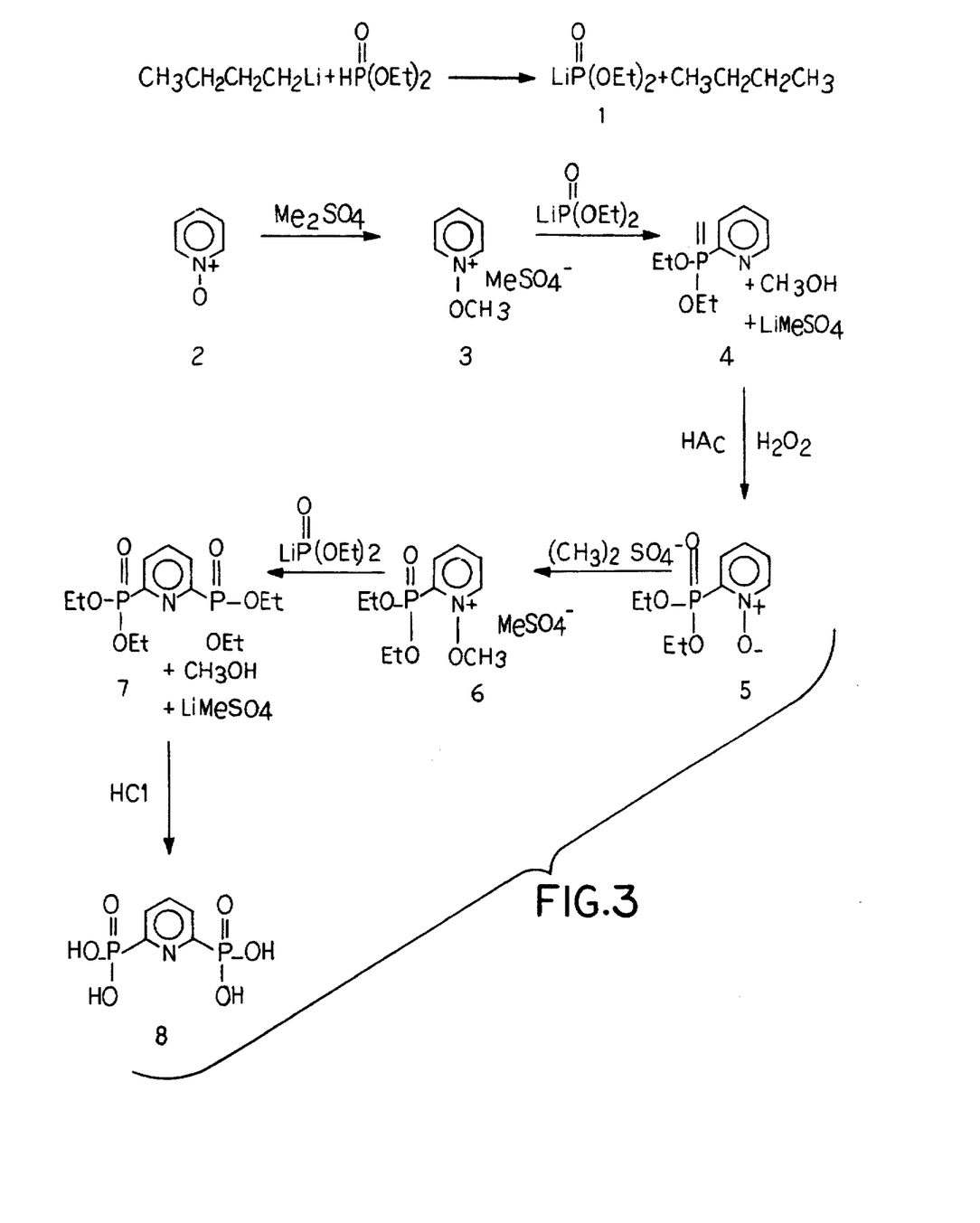
FIG. 3 schematically illustrates another synthesis scheme used to create a preferred embodiment of this invention.

To prepare compound 7 the same procedure as used in the preparation of compound 4 is used. Compound 7 (3.0 g) is next heated under reflux with 30 ml of 6 M HCl for 12 hr. The solvent is removed by evaporation under reduced pressure, and a yellow oil is obtained. Addition of methanol yields a yellow solid which is then recrystallized three times from methanol. The sample of pure product 2,6-pyridinediphosphonic acid, compound 8, is obtained.

Although the above-described syntheses are presented in great detail, there exists many alternative routes that allow these novel ligands to be prepared and subsequently used in catalyst compositions in combination with polyvalent metals. Further, the invention thus far has been described with particular emphasis on the use of iron as the polyvalent metal of choice, however, other polyvalent metals that form chelates with the novel ligands described above can also be used. Such additional polyvalent metals include copper, cobalt, vanadium, manganese, platinum, tungsten, nickel, mercury, tin and lead.

The chelated metal catalyst solution of the present invention is preferably prepared by dissolving a suitable polyvalent metal salt in water, separately dissolving the chelating agent in water, and mixing the two solutions to provide a concentrate. The pH of the concentrate is adjusted by adding the required amount of an alkaline material, such as sodium hydroxide or sodium carbonate, to provide a concentrate of desired neutral or alkaline pH. An appropriate amount of the concentrate can be diluted with water as required to obtain the desired amount of operating solution having the desired polyvalent metal content. The polyvalent metal content of the operating solution can vary over a wide range, dependent upon the gas being treated and other factors. Typically, when an iron chelate catalyst is used, the iron content of the operating solution may be from about 5 ppm to about 5000 ppm, with 200 to 2000 ppm being preferred, although in some applications the iron content can be >5000 ppm. The amount of chelating agent should be at least sufficient to chelate all of the iron in the solution and preferably somewhat in excess of that amount.

In a preferred embodiment the chelating agents of this invention are used in sufficient amount so that the polyvalent metal is chelated predominantly with two moles of the chelating agents per mole of polyvalent metal. The mole ratio of chelating agent to iron should be at least about 2:1 to ensure that substantially all of the polyvalent metal is present as the dimer form of the chelating agent-metal complex, although acceptable results are obtained at less than the 2:1 ratio.

Although the art is replete with different processing flow schemes and conditions to effect the conversion of $H_2S$ to solid sulfur, none of the known processes have utilized the catalysts of this invention. Any of the various methods well known in the art can be used to effect the required intimate contact between the hydrogen sulfide-containing gas and the aqueous catalyst solution, including an aerobic system in which the oxidation of hydrogen sulfide and the regeneration of the catalyst solution are carried out simultaneously in the same reaction vessel. Alternately, an anaerobic system can be used where oxidation of hydrogen sulfide and regeneration of the catalyst solution are effected in separate vessels or reaction zones. Reference is made to the Thompson U.S. Pat. No. 4,189,462 patent for a detailed explanation of the two types of processing systems. In addition, the oxidation-reduction processes disclosed in Hardison U.S. Pat. Nos. 5,139,753 and 5,160,714 describe alternative processes that can use the novel compositions of this invention. Also suitable for practicing this invention is the autocirculation process described in the Hardison U.S. Pat. No. 4,238,462 and the Mancini et al. U.S. Pat. No. 4,011,304 which describes a control system for use in such a process. The Thompson, Hardison and the Mancini et al. patents are all incorporated herein by reference.

The contacting of the hydrogen sulfide-containing gas with the operating solution in the hydrogen sulfide oxidation step is often carried out at ambient conditions of temperature and pressure, but temperatures of from about 5° to about 65° C. and pressures ranging from subatmospheric to 100 atmospheres or greater can be used. A pH ranging from about 5.5 to about 10.5 is usually maintained, although higher pH can be used. In an anaerobic system the regeneration of the reduced catalyst solution is effected by contacting the catalyst solution with air or other oxygen-containing gas at ambient conditions, although higher pressures and lower temperatures can be employed in some circumstances.

Although remarkably stable operations are obtained using the chelated-polyvalent metal catalyst of this invention, an even more stable operation is possible through the use of well known chemical stabilizers, for example, ammonium thiosulfate, alkali metal thiosulfates, alkaline earth metal thiosulfates, ammonium thiosulfate and thiosulfate ion precursors. In addition to the alkaline thiosulfates, certain lower molecular weight aliphatic alcohols may also be used as stabilizing additives to retard or prevent chelate degradation in accordance with the present invention. Preferred materials in this category are the monohydroxy alcohols having 3 to 5 carbon atoms, particularly the alcohols such as t-butanol and isopropanol. The dihydroxy alcohols such as ethylene glycol and propylene glycols may also be used. The concentration of the alcohol additives in the operating solution may be from about 20 to about 100 g/L. The McManus et al. U.S. Pat. No. 4,622,212 describes in detail the nature and chemical effects of these stabilizers and is incorporated herein by reference. To more fully describe the invention the following specific example is presented but is not to be construed as limiting the scope of the invention. As will be understood by those skilled in the art, the solutions or mixtures employed to practice this invention may contain other materials or additives for select given purposes. For example, the use of buffering agents, microbiological growth control agents, antifoaming additives and wetting agents may be employed, as well as other specific additives for simultaneous treatment of organic sulfur species, such as, COS and $CS_2$.

EXAMPLE

The degradation resistances of pyridine-2-phosphonic-6-carboxylic acid (2P6C) and pyridine-2,6-diphosphonic acid (2,6-PDPA), prepared by the synthesis schemes presented in FIGS. 2 and 3, respectively, were evaluated as described below. Both ligands were evaluated in the iron chelate form.

A. DEGRADATION WITHOUT STABILIZATION

1. Degradation of Fe(III)-2P6C at pH 8.5 and 25° C. (Fe(III)0.018M, 2P6C 0.036 M; $H_2S$ flow rate=2.0 mL/min.)

The redox reaction was carried out in a continuous glass reaction apparatus as described in D. Chen, R. J. Motekaitis, A. E. Martell and D. McManus, Can. J. Chem., 71, 1524 (1993) which is incorporated herein by reference.

Preparation of iron-free sample. To 4.0 mL of solution taken from the continuous reactor, 100 mg of NaOH in 20 mL water were added dropwise with stirring. The mixture was heated to 70°–80° C. for 30 min. The $Fe(OH)_3$ that precipitated was filtered off carefully and was washed several times with water. The filtrate was combined with the washings and was transferred to a 50 mL volumetric flask. The pH of the solution was adjusted with acid to 4.2, and then diluted with distilled water to 50 mL.

Operating conditions. Analytical column: I-SIL 5 C8, reverse phase 4.5×150 mm; Column temperature: ambient; mobile phase flow rate: 1.5 mL/min; Detector: UV at 275 nm, 0.20 AUFS; Sample volume: 20 microliter; Recorder: 10 mV full-scale; Chart speed: 0.5 cm/min. The mobile phase contained: 0.0010 M Cu(II), 60:40 $H_2O$: MeOH, 2% HOAc, 0.2% $CH_3(CH_2)_{15}$ $(CH_3)_3NBr$, adjusted to pH 4.2 With NaOH solution.

Figure 4:
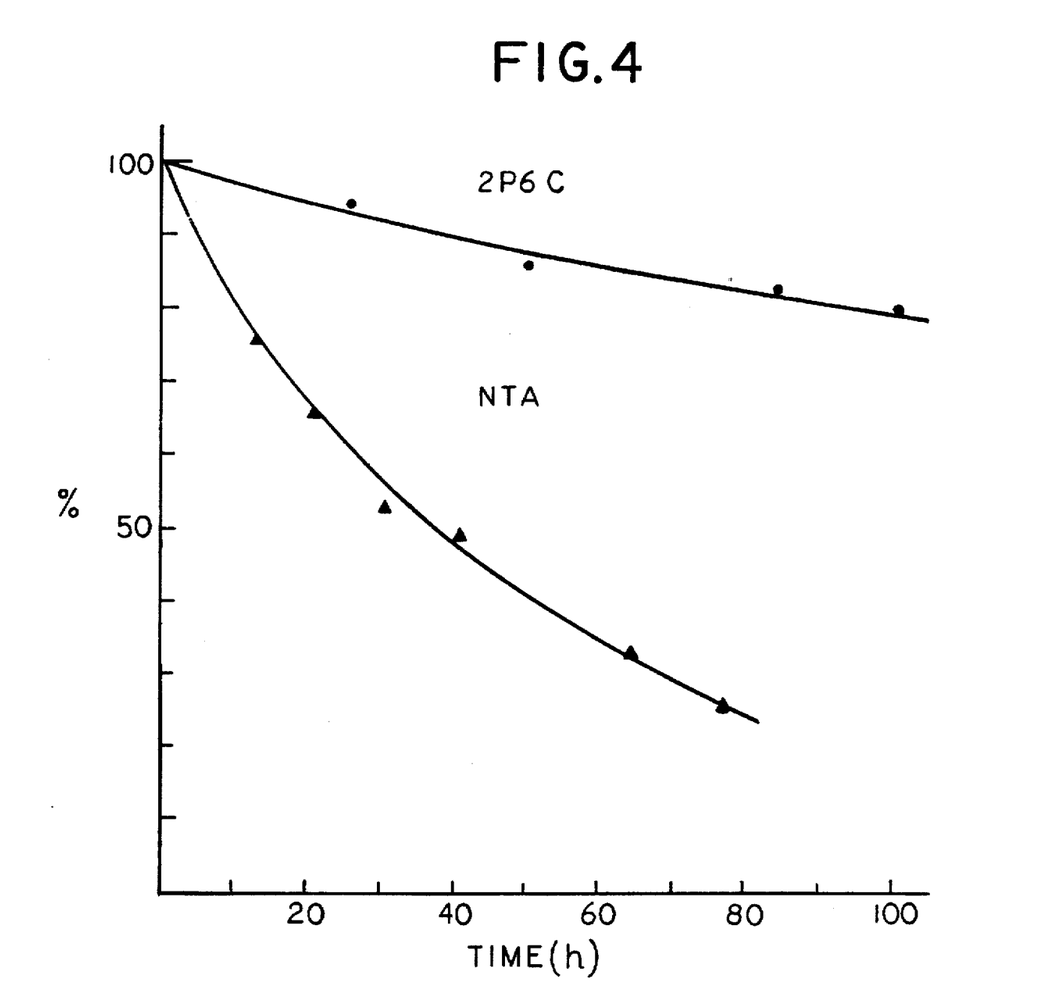
FIG. 4 graphically compares the degradation of two iron chelate catalysts; Fe(III)-2P6C and Fe(III)-NTA in the absence of stabilizer.

The degradation of Fe(III)-2P6C is shown in Table 1 and FIG. 4. The results show that 2P6C degrades very slowly during the redox reaction. After the redox reaction was carried out for 100 hr about 20% of the 2P6C was lost, presumably by hydroxylation. Hydroxylation of the pyridine ring does not significantly, adversely affect the chelating ability of the 2P6C, hence no deleterious effect on the process is observed.

TABLE 1

Degradation of Fe(III)-2P6C at pH 8.5 and 25° C.
(Fe(III) 0.018 M, 2P6C 0.036 M

| Time, hr | 2P6C M | 2P6C % Remaining |
|---|---|---|
| 0 | 0.036 | 100.0 |
| 25 | 0.034 | 94.4 |
| 50 | 0.031 | 86.1 |
| 84 | 0.030 | 83.3 |
| 100 | 0.029 | 80.6 |

2. Degradation of Fe(III)-2,6 PDPA at pH 8.5 and 25° C.: Fe(III) 0.0090 M; 2,6 PDPA 0.018 M and 25° C., $H_2S$ flow rate=2.0 mL/min.)

The concentration of 2,6 PDPA was analyzed by the following uv-vis spectrophotometric measurements: to 1.0 mL of solution taken from the continuous reactor, 150 mg of NaOH in 15 mL water was added with stirring. The mixture was heated with a steam-bath for 2 hr, then allowed to stand at room temperature for 2 hr. The $Fe(OH)_3$ that precipitated was filtered off carefully and washed several times with water. The filtrate combined with the washings, was transferred to a 50 mL volumetric flask, and diluted to 10 mL with 6M HCl. This solution was ready for uv-vis spectrophotometric analysis.

The results show that after the redox reaction was carried out for 100 hr, no significant degradation was observed. On the basis of the results obtained the degradation of 2,6 PDPA is estimated to be less than 5% over a 100 hr period of operation.

3. Degradation of NTA

Using the same test conditions described above, the degradation of nitrilotriacetic acid (NTA) was evaluated. Table 2 and FIG. 4 compares the measured rate of degradation of 2P6C and NTA iron chelate systems starting with the same concentration of Fe(III) in each case. It is obvious from FIG. 4 that 2P6C degrades much more slowly than NTA.

TABLE 2

Degradation of Fe(III)-NTA at pH 8.5.

| Time, hr | NTA (M) | NTA, % Remaining |
|---|---|---|
| 0 | 0.0362 | 100.0 |
| 12.0 | 0.0274 | 75.7 |
| 20.0 | 0.0238 | 65.7 |
| 30.0 | 0.0190 | 52.4 |
| 40.0 | 0.0179 | 49.4 |
| 64.0 | 0.0119 | 32.9 |
| 77.0 | 0.0095 | 26.2 |

B. DEGRADATION IN THE PRESENCE OF STABILIZER

1. Nitrilotriacetic Acid (NTA)

Figure 5:
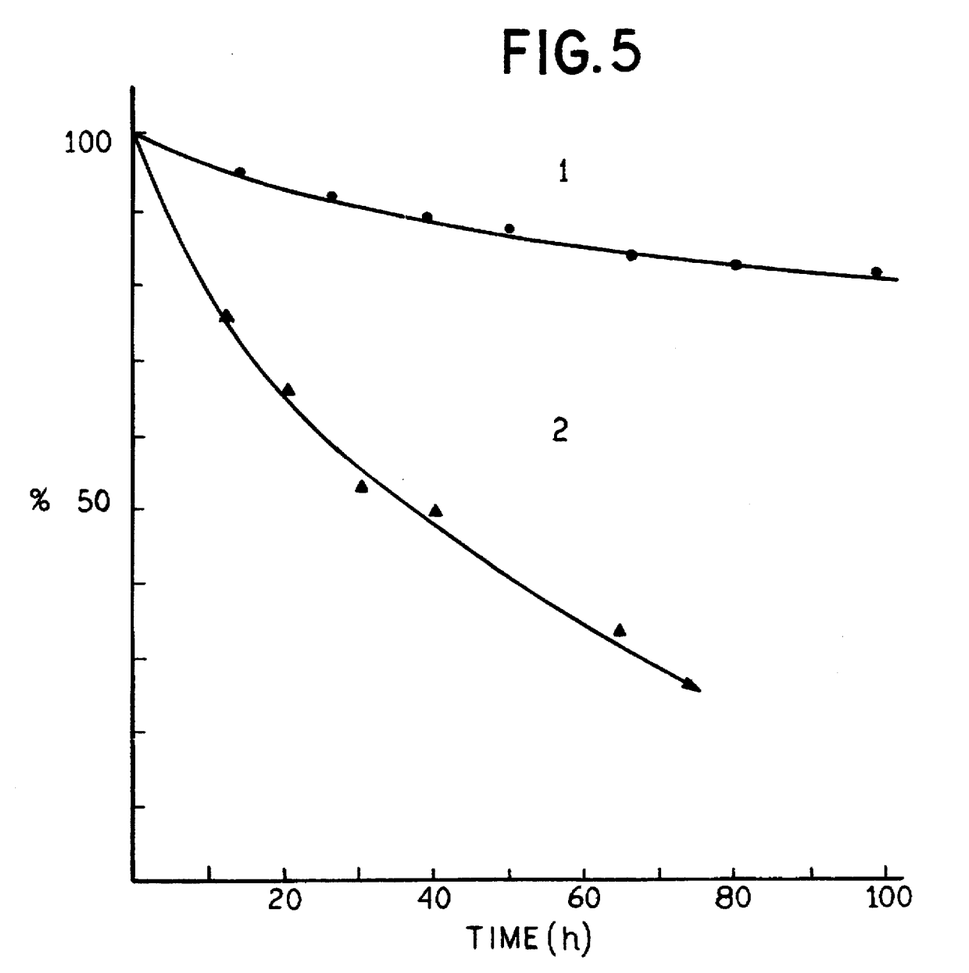
FIG. 5 graphically illustrates the degradation of Fe(III)-NTA with and without $Na_2S_2O_3 \cdot 5H_2O$ stabilizer.

Degradation of NTA is much slower when thiosulfate is added to scavenge the radical oxidant, probably the hydroxyl radical, which is considered responsible for the oxidative degradation of NTA. Table 3 and FIG. 5 contain the data obtained from a run with the continuous glass reaction apparatus described above.

TABLE 3

Degradation of Fe(III)-NTA at pH 8.5 with 32 g $Na_2S_2O_3$ (per liter)

| Time hr | NTA (M) | NTA, % Remaining |
|---------|---------|------------------|
| 0       | 0.0362  | 100.0            |
| 14.0    | 0.0344  | 95.0             |
| 26.0    | 0.0333  | 92.0             |
| 39.0    | 0.0320  | 88.4             |
| 50.0    | 0.0317  | 87.6             |
| 66.0    | 0.0306  | 84.5             |
| 80.0    | 0.0297  | 82.0             |
| 99.0    | 0.0293  | 80.9             |

2. The Phosphonate Ligands

When similar degradation runs were carried out with 2P6C and 2,6 PDPA in the presence of thiosulfate, no detectable degradation was observed after 100 hr of operation. Experimental runs were also conducted with 2P6C, with and without $K_2SO_3$ added as a stabilizer. Tables 4, and FIG. 6, illustrate the improvement in stability.

TABLE 4

| Time, hr | 2P6C M | 2P6C, 5% $K_2SO_3$ % Remaining |
|----------|--------|-------------------------------|
| 0        | 0.036  | 100.0                         |
| 2        | 0.036  | 100.0                         |
| 20       | 0.035  | 97.7                          |
| 44       | 0.035  | 97.6                          |
| 68       | 0.035  | 97.4                          |
| 92       | 0.036  | 98.9                          |

Therefore it is seen that thiosulfate lowers the rate of degradation of all three chelating agents, however, the rate of degradation of NTA is still measurable. The rates of degradation of the phosphonates are virtually unmeasurable.

We claim:

1. A metal chelate composition having the following formula: $ML_2$ where, (a) L has the following formula:

(b) R is COOH or $PO(OH)_2$;

(c) $R_1$, $R_2$ and $R_3$ are each selected independently from the group consisting of H, OH, alkyl containing 1 through 3 carbon atoms, $NO_2$, $SO_3H$, Cl, Br, F, and CN; and (d) M is a polyvalent metal that exists in more than one oxidation state.

2. A metal chelate composition having the following formula: ML where, (a) L has the following formula:

(b) R is COOH or $PO(OH)_2$;

(c) $R_1$, $R_2$ and $R_3$ are each selected independently from the group consisting of H, OH, alkyl containing 1 through 3 carbon atoms, $NO_2$, $SO_3H$, Cl, Br, F, and CN; and (d) M is a polyvalent metal that exists in more than one oxidation state.

3. The composition of claim 1 wherein M is selected from the group consisting of iron, copper, cobalt, nickel and manganese.

4. The composition of claim 1 wherein M is iron.

5. The composition of claim 2 wherein M is selected from the group consisting of iron, copper, cobalt, nickel and manganese.

6. The composition of claim 2 wherein M is iron.

* * * * *